(12) United States Patent
Takamatsu et al.

(10) Patent No.: US 9,954,162 B2
(45) Date of Patent: Apr. 24, 2018

(54) REACTIVE IONIC LIQUID, AND ION-IMMOBILIZED METAL OXIDE PARTICLE, ION-IMMOBILIZED ELASTOMER, AND TRANSDUCER USING SAME

(71) Applicants: SUMITOMO RIKO COMPANY LIMITED, Aichi-ken (JP); KYUSHU UNIVERSITY, Fukuoka (JP)

(72) Inventors: Shigeaki Takamatsu, Aichi-ken (JP); Yota Kokubo, Aichi-ken (JP); Kazunobu Hashimoto, Aichi-ken (JP); Hitoshi Yoshikawa, Aichi-ken (JP); Atsushi Takahara, Fukuoka-ken (JP); Ryousuke Matsuno, Saga-ken (JP); Hideyuki Otsuka, Kanagawa (JP)

(73) Assignees: SUMITOMO RIKO COMPANY LIMITED, Aichi-Ken (JP); KYUSHU UNIVERSITY, Fukuoka (JP)

( * ) Notice: Subject to any disclaimer, the term of this patent is extended or adjusted under 35 U.S.C. 154(b) by 668 days.

(21) Appl. No.: 14/573,658

(22) Filed: Dec. 17, 2014

(65) Prior Publication Data

US 2015/0137666 A1    May 21, 2015

Related U.S. Application Data

(63) Continuation of application No. PCT/JP2014/057515, filed on Mar. 19, 2014.

(30) Foreign Application Priority Data

Mar. 25, 2013 (JP) ................. 2013-061430

(51) Int. Cl.
*H01L 41/193* (2006.01)
*C07F 9/6506* (2006.01)
(Continued)

(52) U.S. Cl.
CPC ............ *H01L 41/193* (2013.01); *C07C 53/10* (2013.01); *C07C 53/18* (2013.01); *C07C 205/06* (2013.01);
(Continued)

(58) Field of Classification Search
CPC ....... H01L 41/193; C07C 53/10; C07C 53/18; C07C 309/06; H04R 17/00; C04B 35/00
(Continued)

(56) References Cited

U.S. PATENT DOCUMENTS 7,671,514 B2 * 3/2010 Lee ........................... F03G 7/00
                                                              310/328
8,981,625 B2 * 3/2015 Nishikubo ............ H01L 41/193
                                                              310/358
(Continued)

FOREIGN PATENT DOCUMENTS

CN      1835957 A      9/2006
CN      1886413 A      12/2006
(Continued)

OTHER PUBLICATIONS

Christian Schnaars et al., "Nucleophilic Halogenations of Diazo Compounds, a Complementary Principle for the Synthesis of Halodiazo Compounds: Experimental and Theoretical Studies", the Journal of Organic Chemistry, 2013, 78, pp. 7488-7497.
(Continued)

*Primary Examiner* — Bryan Gordon
(74) *Attorney, Agent, or Firm* — Greenblum & Bernstein, P.L.C.

(57) ABSTRACT

A reactive ionic liquid to be used as an ionic component that is contained in an ion-containing layer in a transducer arranged in contact with a high-resistance layer as a dielectric layer of the transducer, and is restrained from migrating from the ion-containing layer to the high-resistance layer on
(Continued)

application of a voltage is provided. The reactive ionic liquid comprises an ion pair that consists of an anion and a cation. (a) The cation (a1) is an imidazolium or quaternary ammonium cation, and (a2) comprises a reactive group that consists of an alkoxysilyl or phosphonate group. (b) The anion (b1) is a sulfonate, sulfonylimide, or nitrobenzoate anion.

10 Claims, 3 Drawing Sheets

(51) Int. Cl.
  C08K 9/04 (2006.01)
  C07C 53/10 (2006.01)
  C07C 53/18 (2006.01)
  C07C 205/06 (2006.01)
  C07C 309/06 (2006.01)
  C07C 309/30 (2006.01)
  C07C 317/04 (2006.01)
  C07F 7/18 (2006.01)
  C07F 7/28 (2006.01)
  C07F 9/40 (2006.01)
  C08F 220/46 (2006.01)
  C08K 9/06 (2006.01)
  H01L 41/09 (2006.01)

(52) U.S. Cl.
  CPC .......... C07C 309/06 (2013.01); C07C 309/30 (2013.01); C07C 317/04 (2013.01); C07F 7/1804 (2013.01); C07F 7/28 (2013.01); C07F 9/40 (2013.01); C07F 9/65061 (2013.01); C08F 220/46 (2013.01); C08K 9/04 (2013.01); C08K 9/06 (2013.01); H01L 41/0986 (2013.01)

(58) Field of Classification Search
  USPC .............................. 310/311, 800, 324, 358
  See application file for complete search history.

(56) References Cited

U.S. PATENT DOCUMENTS

| | | | |
|---|---|---|---|
| 2002/0122561 A1 | 9/2002 | Pelrine et al. | |
| 2007/0021615 A1 | 1/2007 | Koehler et al. | |
| 2011/0025963 A1* | 2/2011 | Nagase | G02B 5/3083 349/117 |
| 2012/0232301 A1 | 9/2012 | Chen et al. | |
| 2013/0142548 A1* | 6/2013 | Suzuki | C08L 83/04 399/286 |
| 2014/0300247 A1* | 10/2014 | Takamatsu | F03G 7/005 310/300 |
| 2014/0370182 A1 | 12/2014 | Umezaki et al. | |

FOREIGN PATENT DOCUMENTS

| | | |
|---|---|---|
| CN | 101838290 A | 9/2010 |
| EP | 1690867 A1 | 8/2006 |
| EP | 2 264 801 | 12/2010 |
| JP | 2003-506858 A | 2/2003 |
| JP | 2007-204560 A | 8/2007 |
| JP | 2009-275022 A | 11/2009 |
| JP | 2011-148641 A | 8/2011 |
| JP | 2011-201104 A | 10/2011 |
| JP | 2001-524278 A | 11/2011 |
| JP | 2011-219852 A | 11/2011 |
| KR | 2013-0044038 A | 5/2013 |
| WO | 2005/016940 A1 | 2/2005 |
| WO | 2010/013822 A2 | 2/2010 |
| WO | 2012/043303 A1 | 4/2012 |
| WO | 2013/011822 A2 | 1/2013 |
| WO | 2013/038901 A1 | 3/2013 |
| WO | 2014/029813 A1 | 2/2014 |

OTHER PUBLICATIONS

Shamsuddeen A. Haladu et al., "A pH-responsive Cyclopolymer Having Phospho- and Sulfopropyl Pendents in the Same Repeating Unit: Synthesis, Characterization, and Its Application as an Antiscalant", Journal of Polymer Science, Part A: Polymer Chemistry 2013, 51, pp. 5130-5142.

Hengquan Yang et al., "Magnetic core-shell-structured nanoporous organosilica microspheres for the Suzuki-Miyaura coupling of aryl chlorides: improved catalytic activity and facile catalyst recovery", J. Mater. Chem., 2012, 22, pp. 6639-6648.

XP-002752774, "Composition for forming silicon-containing resist underlayer film with onium group".

Simona M Coman et al., "Metal-triflate ionic liquid systems immobilized onto mesoporous MS41 materials as new and efficient catalysts for N-acylation", Journal of Catalysis, 249, 2007, pp. 359-369.

Hengquan Yang et al., "Three-dimensional cubic mesoporous materials with a built-in N-heterocyclic carbene for Suzuki-Miyaura coupling of aryl chlorides and C(sp3)-chlorides", Journal of Catalysis, 276, 2010, pp. 123-133.

Thy Phuong Nguyen et al., "Periodic mesoporous organosilica containing ionic bis-aryl-imidazolium entities: Heterogeneous precursors for silica-hybrid-supported NHC complexes", J. Mater. Chem., 2009, 19, pp. 4164-4171.

H. Gross et al., "P-C-Spaltungen bei geminalen Trisphosphorylverbindungen", Journal prakt. Chem., 328, 1986, pp. 231-236.

Dorota G. Piotrowska et al., "Direct observation of aziridinium ions in a 2-(N,N-dibenzylamino)- to 1-(N,N-dibenzylamino)phosphonate rearrangement", Tetrahedron, 65, 2009, pp. 4310-4315.

M. D. R. Gomes da Silva et al., "New chiral imidazolium ionic liquids from isomannide", Carbohydrate Research, 346, 2011, pp. 197-202.

XP-002752775, "Nanoparticle/dispersant complex, nanoparticle dispersion liquid, and nanoparticle/matrix-material complex".

XP-002752776, "Sulfo- and silyl-containing imidazolium inner salts, their preparation, oxide particles supporting the salts thereon, and uses of the supported salts as catalysts".

European Search Report issued with respect to application No. 14775704.1, dated Mar. 7, 2016.

Chinese Office Action issued with respect to application No. 201480003518.9, dated Mar. 3, 2017.

European Office Action issued with respect to application No. 14775704.1, dated Oct. 25, 2016.

A. Rout et al., "Unusual extraction of plutonium (IV) from uranium (VI) and americium (III) using phosphonate based task specific ionic liquid", Radiochim Acta, 2010, pp. 459-466, vol. 98, No. 8.

Search report from PCT/JP2014/057515, dated May 27, 2014.

Chinese Office Action issued with respect to application No. 201480003518.9, dated Aug. 3, 2016.

Japanese Office Action issued with respect to application No. 2014-548224, dated Oct. 27, 2015.

* cited by examiner

REACTIVE IONIC LIQUID, AND ION-IMMOBILIZED METAL OXIDE PARTICLE, ION-IMMOBILIZED ELASTOMER, AND TRANSDUCER USING SAME

CLAIM FOR PRIORITY

This application is a Continuation of PCT/JP2014/057515 filed Mar. 19, 2014, and claims the priority benefit of Japanese application 2013-061430, filed Mar. 25, 2013, the contents of which is expressly incorporated by reference herein in its entirety.

TECHNICAL FIELD

The present invention relates to a reactive ionic liquid, and an ion-immobilized metal oxide particle, an ion-immobilized elastomer, and a transducer using the same.

BACKGROUND ART

Transducers such as an actuator, a sensor, and a power generating device perform conversion between mechanical energy and electric energy. Another type of transducers such as a speaker and a microphone perform conversion between acoustic energy and electric energy. In order to form a highly flexible, compact, and lightweight transducer, polymer materials such as dielectric elastomers are useful.

For example, an actuator may contain a dielectric layer formed of a dielectric elastomer and a pair of electrodes placed on both sides of the dielectric layer in the thickness direction. In the actuator, when a voltage applied between the electrodes is increased, an electrostatic attraction between the electrodes increases. The dielectric layer, placed between the electrodes, is thereby compressed in the thickness direction, leading to a reduced thickness of the dielectric layer. When the film thickness is reduced, the dielectric layer accordingly expands in a direction parallel to the electrode surfaces. On the other hand, when the voltage applied between the electrodes is reduced, the electrostatic attraction between the electrodes decreases. A compressive force applied to the dielectric layer in the thickness direction thereby decreases, and the film thickness increases due to the elastic restoring force of the dielectric layer. When the film thickness increases, the dielectric layer accordingly contracts in the direction parallel to the electrode surfaces. The actuator thus expands and contracts its dielectric layer, thereby actuates a member to be actuated.

In order to increase the force and displacement that are output from the actuator, it is preferable that the dielectric layer has a higher dielectric constant, higher resistance to dielectric breakdown, and higher flexibility. A higher dielectric constant allows the layer to accumulate more charges therein under application of a voltage. Higher resistance to dielectric breakdown allows the layer to withstand a higher electric field. Higher flexibility allows the layer to be expanded and contracted repeatedly. A silicone rubber, which has high resistance to dielectric breakdown, and acrylic and nitrile rubbers, which have high dielectric constants, are frequently used to prepare the dielectric layer (see, for example, PTL1 and PTL2).

CITATION LIST

Patent Literature

PTL1: JP 2003-506858 A
PTL2: JP 2001-524278 A
PTL3: JP 2011-201104 A

SUMMARY OF INVENTION

Technical Problem

A silicone rubber has a backbone consisting of siloxane bonds, which provides a high electric resistance. Thus, a dielectric layer made of a silicone rubber is hard to be dielectrically broken down when a high voltage is applied to the layer. However, the silicone rubber has a low polarity, and thus has a low dielectric constant. Consequently, when the dielectric layer of the actuator is made of the silicone rubber, the electrostatic attraction between the electrodes with respect to the applied voltage is small. It is therefore difficult to obtain desired force and displacement by application of a practical voltage.

Meanwhile, acrylic and nitrile rubbers have higher dielectric constants than the silicone rubber. Thus, when the dielectric layer is made of the acrylic or nitrile rubber, the electrostatic attraction between the electrodes with respect to the applied voltage is larger, compared to a case where the silicone rubber is used. However, the acrylic and nitrile rubbers have lower electric resistances than the silicone rubber. Therefore, the dielectric layer is more susceptible to dielectric breakdown. Further, an electric current (i.e., so-called a leakage current) passes through the dielectric layer during voltage application, and thus electric charges are hard to be stored in the vicinity of the interface between the dielectric layer and the electrodes. Therefore, despite the high dielectric constants of the acrylic and nitrile rubbers, the electrostatic attraction decreases, and thus a satisfactory force and displacement can not be obtained. Furthermore, there is a risk that when a current passes through the dielectric layer, the dielectric layer may be physically broken due to generated Joule heat.

Thus, it is difficult to realize a dielectric layer providing both a large generative force and high resistance to dielectric breakdown with the use of a single material. A dielectric layer has been proposed which is made of a plurality of materials in combination to provide both satisfactory generative force and satisfactory resistance to dielectric breakdown.

For example, PTL3 discloses a dielectric laminate that comprises an ion-containing layer and a high-resistance layer. The ion-containing layer contains an elastomer and an ion component while the high-resistance layer contains an elastomer and has a higher volume resistivity than the ion-containing layer.

In the dielectric laminate disclosed in PTL3, however, there is a possibility that the high-resistance layer is subjected to dielectric breakdown since the ion component in the ion-containing layer easily migrates into the high-resistance layer. Thus, in the dielectric laminate, it is desired that the ion component is prevented from migrating into the high-resistance layer.

The present invention has been made in view of the problems described above, and an object of the present invention is to provide a reactive ionic liquid to be used as an ionic component that is contained in an ion-containing layer in a transducer arranged in contact with a high-resistance layer as a dielectric layer of the transducer, and is restrained from migrating from the ion-containing layer to the high-resistance layer on application of a voltage. Another object of the present invention is to provide an ion-immobilized metal oxide particle, an ion-immobilized elastomer, and a transducer, using the reactive ionic liquid.

Solution to Problem

To achieve the objects and in accordance with the purpose of the present invention, a reactive ionic liquid according to a preferred embodiment of the present invention comprises anion pair that consists of an anion and a cation. In the reactive ionic liquid, (a) the cation (a1) is an imidazolium or quaternary ammonium cation, and (a2) comprises a reactive group that consists of an alkoxysilyl or phosphonate group. (b) The anion (b1) is a sulfonate, sulfonylimide, or nitrobenzoate anion.

The cation preferably has a structure represented by one selected from general formulae (1) to (3):

where, in formulae (1) to (3), $R_1$ to $R_{11}$ are straight-chain or branched alkyl groups that either comprise or do not comprise heteroatoms, and at least apart of the plurality of $R_4$ are either identical to and or different from one another.

In another aspect of the present invention, an ion-immobilized metal oxide particle according to a preferred embodiment of the present invention comprises the cation of the reactive ionic liquid described above and a metal oxide particle comprising a hydroxyl group. The cation is immobilized to the metal oxide particle via an Si—O or P—O bond between the reactive group of the cation and the hydroxyl group of the metal oxide particle.

In another aspect of the present invention, an ion-immobilized elastomer according to a preferred embodiment of the present invention comprises the ion-immobilized metal oxide particle described above and an elastomer that comprises a functional group that is reactive with a hydroxyl group. The ion-immobilized metal oxide particle is immobilized to the elastomer via a bond between a hydroxyl group contained in the ion-immobilized metal oxide particle and the functional group contained in the elastomer.

In another aspect of the present invention, a transducer according to a preferred embodiment of the present invention comprises a high-resistance dielectric layer that comprises an elastomer and has a volume resistivity of $10^{13}$ ••cm or higher, a pair of positive and negative electrodes that are arranged on front and back sides of the high-resistance dielectric layer, and an ion-immobilized layer arranged between the high-resistance dielectric layer and the positive electrode. The ion-immobilized layer comprises the ion-immobilized elastomer described above.

Advantageous Effects of Invention

Since the reactive ionic liquid according to the preferred embodiment of the present invention has the alkoxysilyl or phosphonate group as the reactive group in the cation, the cation can be immobilized to a metal oxide particle that has a hydroxyl group. The metal oxide particle to which the cation of the reactive ionic liquid is immobilized can be immobilized to an elastomer that has a functional group that is reactive with a hydroxyl group, by a reaction between the hydroxyl group contained in the ion-immobilized metal oxide particle and the functional group contained in the elastomer. Thus, the cation of the reactive ionic liquid is immobilized to the elastomer via the metal oxide particle. When an ion-containing layer that is in contact with a high-resistance layer as a dielectric layer in a transducer is made of the elastomer, the cation contained in the ion-containing layer is restrained from migrating into the high-resistance layer since the cation is immobilized in the ion-containing layer. Thus, dielectric breakdown of the high-resistance layer is suppressed.

DESCRIPTION OF EMBODIMENTS

A detailed description of a preferred embodiment of the present invention will now be provided.

A reactive ionic liquid according to a preferred embodiment of the present invention contains an ion pair that consists of a specific cation and a specific anion.

The cation of the reactive ionic liquid is an imidazolium or quaternary ammonium cation, and has an alkoxysilyl group (—Si(OR)$_3$) or a phosphonate group (—P(=O)(OR)$_2$) as a reactive group. Here, R represents an alkyl or aryl group.

The cation having the alkoxysilyl group (—Si(OR)$_3$) or the phosphonate group (—P(=O)(OR)$_2$) easily reacts with, for example, a compound having a hydroxyl group to form an Si—O or P—O bond, respectively. Thus, the cation of the reactive ionic liquid, having the reactive group, can be immobilized to a compound having a hydroxyl group such as a metal oxide particle via the Si—O or P—O bond.

The cation of the reactive ionic liquid is not particularly limited as long as it is an imidazolium or quaternary ammonium cation having at least one of the above-described reactive groups. Containing the cation, the reactive ionic liquid has a high reactivity with a hydroxyl group. The higher the reactivity is, the more effectively the cation is immobilized to a compound having a hydroxyl group such as a metal oxide particle.

It is preferable that the cation of the reactive ionic liquid does not have a substituent group that tends to provide steric hindrance or an intramolecular reactive group, in view of increasing the reactivity of the reactive group.

The cation preferably has a structure represented by one of general formulae (1) to (3) below, for example.

In formulae (1) to (3), $R_1$ to $R_{11}$ represent straight-chain or branched alkyl groups. The number of carbon atoms in each of the alkyl groups is preferably within a range of 1 to 4. Each of alkyl groups $R_1$ to $R_{11}$ may contain a heteroatom (such as N, O, and S). A part or all of the plurality of $R_4$ may be different from one another.

Specific examples of the cation represented by formula (1) include the cations represented by formulae (4) and (5). Specific examples of the cation represented by formula (2) include the cations represented by formulae (6) to (8). Specific examples of the cation represented by formula (3) include the cations represented by formulae (9) and (10). Among them, a cation that provides smaller steric hindrance is preferable to be contained in the reactive ionic liquid because of a higher reactivity thereof. The strength of ion-ion interaction between each of the cations represented by formulae (4) to (10) and the anion is in an order of (4)>(7)>(6)/(9)>(5)>(8)/(10), though the strength also depends on the type of the anion. The maximum positive charge on a surface of a dielectric material containing the reactive ionic liquid increases in the above-presented order.

The anion of the reactive ionic liquid is selected from sulfonate, sulfonylimide, and nitrobenzoate anions. Specific examples of the anion include $CF_3SO_3^-$, $CH_3SO_3^-$, $CH_3C_6H_4SO_3^-$, $C_6H_5SO_3^-$, $(CF_3SO_2)_2N^-$, 3-nitrobenzoate anion, and 4-nitrobenzoate anion. They provide relatively weak ion-ion interaction with the cation, and thus enhance the ionic property of the reactive ionic liquid. The anions listed above allow a dielectric material containing the reactive ionic liquid to have a dielectric constant ($\in$) of 1000 or higher at a frequency of 0.01 Hz, thought the dielectric constant also depends on the type of the cation. $CF_3SO_3^-$, $CH_3SO_3^-$, $C_6H_5SO_3^-$, and $CH_3C_6H_4SO_3^-$ are especially preferable among the anions listed above because they are relatively small ions and thus have high reactivities due to steric factors. $CF_3SO_3^-$, $C_6H_5SO_3^-$, and $CH_3C_6H_4SO_3^-$ are more preferable. $CF_3SO_3^-$ is preferable because the anionic charge thereof is weakened by the fluoro group, which is electrophilic. Thus, $CF_3SO_3^-$ provides a decreased ion-ion interaction with the cation and an increased ionic property of the reactive ionic liquid. $C_6H_5SO_3^-$ and $CH_3C_6H_4SO_3^-$ are preferable because the anions have phenyl groups, which are electrophilic, too, and because the anions provide high ion retention rates when the ionic liquids containing the anions are immobilized.

Examples of the anion of the reactive ionic liquid also include $CF_3CO_2^-$ and $CH_3CO_2^-$. The anions have higher reactivities, though dielectric materials that contain reactive ionic liquids containing the cations have relatively low dielectric constants ($\in$) of lower than 100 at a frequency of 0.01 Hz, and thus the reactive ionic liquids have lower ionic properties. The strength of ion-ion interaction between each of the anions and the cation is in an order of $CH_3CO_2^->CF_3CO_2^-/CH_3SO_3^->$3-nitrobenzoate anion>4-nitrobenzoate anion>$CH_3C_6H_4SO_3^->C_6H_5SO_3^->CF_3SO_3^->(CF_3SO_2)_2N^-$. The maximum positive charge on a surface of a dielectric material containing the reactive ionic liquid increases in the above-presented order.

The reactive ionic liquid according to the preferred embodiment of the present invention may be synthesized by an anion exchange method or an acid ester method from a known salt compound. In the anion exchange method, a known salt compound having a halogen as an anion is used. The halogen in the compound is replaced with a desired anion. In the acid ester method, a known salt compound having a carbonate ester as an anion is used. The carbonate ester in the compound is replaced with a desired anion.

The reactive ionic liquid containing the cation represented by general formula (1) or (2) has a sulfide group in the structure thereof. Thus, the ionic liquid may be synthesized by an ene-thiol reaction between a compound that has an ene structure in a cationic moiety thereof and a thiol compound. The ene-thiol reaction is an effective reaction in which side reactions are suppressed. Further, since a metal catalyst such as a platinum catalyst is not used in the ene-thiol reaction, there is no possibility that a metal atom remains in the obtained reactive ionic liquid and affects properties of a product containing the reactive ionic liquid such as a transducer. A specific functional group may be introduced into the cationic moiety with the use of a thiol compound having the specific functional group in the ene-thiol reaction.

Next, a description of an ion-immobilized metal oxide particle according to a preferred embodiment of the present invention will be provided.

In the ion-immobilized metal oxide particle, the cation of the reactive ionic liquid according to the preferred embodiment of the present invention is immobilized to a metal oxide particle via a Si—O or P—O bond between the reactive group of the cation and a hydroxyl group contained in the metal oxide particle.

The metal oxide particle, in view of having a high insulating property, preferably contains at least one element selected from titanium, zirconium, and silicon. Examples of the metal oxide particle include single oxide particles such as titanium dioxide ($TiO_2$), zirconium dioxide ($ZrO_2$), silica ($SiO_2$), and barium titanate particles. The examples also include composite oxide particles such as $TiO_2/ZrO_2$ and $TiO_2/SiO_2$ particles. The metal oxide particle is preferably prepared by hydrolysis of an organometallic compound (i.e., sol-gel reaction) because the method facilitates formation of the ion-immobilized metal oxide particle.

The ion-immobilized metal oxide particle may be synthesized by a reaction of the metal oxide particle prepared by the sol-gel reaction with the reactive ionic liquid according to the preferred embodiment of the present invention.

An organometallic compound may be used as a starting material for the sol-gel reaction. The organometallic compound used in the sol-gel reaction is preferably chelated. Chelating of the organometallic compound suppresses a rapid reaction of the organometallic compound with water, whereby metal oxide particles having small diameters are produced without being aggregated.

The organometallic compound may be appropriately selected from metal alkoxide compounds and metal acylate compounds depending on the type of the metal oxide particle to be prepared. Examples of the metalalkoxide compounds include tetra-n-butoxy titanium, tetra-n-butoxy zirconium, tetra-n-butoxy silane, tetra-i-propoxy titanium, tetraethoxysilane, tetrakis(2-ethylhexyloxy) titanium, and titanium butoxide dimer. Examples of the metal acylate compounds include polyhydroxy titanium stearate and zirconium tributoxy monostearate.

Examples of a chelating agent include a β-diketone such as acetylacetone, benzoylacetone, and dibenzoylmethane; a β-keto acid ester such as ethyl acetoacetate and ethyl benzoylacetate; triethanolamine; lactic acid; 2-ethylhexane-1,3-diol; and 1,3-hexanediol.

In the sol-gel reaction, the reactive ionic liquid, an organic solvent, and water are added to the chelated organometallic compound. The hydrolysis of the organometallic compound thereby proceeds to produce a metal oxide particle. The produced metal oxide particle has a hydroxyl group.

Hydroxyl group reacts with the alkoxysilyl group ($-Si(OR)_3$) or the phosphonate group ($-P(=O)(OR)_2$), which is the reactive group of the cation of the reactive ionic liquid. By the reaction, the cation of the reactive ionic liquid is immobilized to the metal oxide particle via a Si—O or P—O bond. The cation is chemically bonded on a surface of or inside the metal oxide particle.

Examples of the organic solvent used in the sol-gel reaction include alcohols such as methanol, ethanol, and isopropyl alcohol (IPA); ketones such as methyl ethyl ketone (MEK) and methyl isobutyl ketone (MIBK); and ethers such as tetrahydrofuran (THF). For example, addition of IPA improves affinity between the chelated compound and water, so that a core for the metal oxide particle is easily produced.

The ion-immobilized metal oxide particle may be used to form a dielectric layer of a transducer or a solid polymer electrolyte, for example, when the particle is immobilized to an organic polymer such as an elastomer.

When used to form a dielectric layer of a transducer, the ion-immobilized metal oxide particle is preferably dispersed in the elastomer as uniformly as possible in view of providing high transparency and resistance to dielectric breakdown of the dielectric layer. The diameter of the ion-immobilized metal oxide particle is preferably as small as possible. The median diameter of the metal oxide particle constituting the ion-immobilized metal oxide particles is preferably 5 nm or larger and 100 nm or smaller. The median diameter is more preferably 30 nm or less, and still more preferably in a range of about 10 nm to 20 nm. The diameter of the metal oxide particle may be measured through observation with a transmission electron microscope (TEM). Alternatively, the diameter may be measured by a small-angle x-ray scattering method.

The diameter of the metal oxide particle to be produced depends on the type and amount of the organic solvent used in the reaction. For example, when a metal oxide particle having a median diameter of about 10 to 20 nm is to be produced, it is preferable that IPA and MEK may be mixed at a molar ratio IPA/MEK=0.6, approximately, while the amount of the IPA is seven to ten times, in molar ratio, of the amount of the organometallic compound. Water may be added as much as required for the hydrolysis of the organometallic compound.

When the metal oxide particle is produced by the hydrolysis of the organometallic compound, the diameter of the metal oxide particle in the sol and the diameter of the metal oxide particle in the dielectric layer are presumably identical. The diameter of the metal oxide particle in the sol may therefore be regarded as the diameter of the metal oxide particle in the dielectric layer. The diameter of the metal oxide particle in the sol may be measured with a laser diffraction/scattering particle diameter/particle size distribution measurement apparatus, manufactured by Nikki so Co., Ltd., for example. Alternatively, the diameter may be measured through observation with a scanning electron microscope (SEM) when the sol is dried.

The sol prepared by the hydrolysis of the organometallic compound contains the anion, which is a counterpart of the cation that is immobilized to the metal oxide particle, as well as the ion-immobilized metal oxide particle.

The sol obtained may be subjected to an aging treatment. The aging treatment may be performed by leaving the sol for several hours at a temperature of about 40° C. The aging treatment reduces the number of the hydroxyl groups remaining in the metal oxide particle, thereby suppressing the aggregation of the ion-immobilized metal oxide particles in the sol under storage.

Next, a description of an ion-immobilized elastomer according to a preferred embodiment of the present invention will be provided.

In the ion-immobilized elastomer, the ion-immobilized metal oxide particle according to the preferred embodiment of the present invention is immobilized to an elastomer that has a functional group reactive with the hydroxyl group contained in the ion-immobilized metal oxide particle, by a reaction between the hydroxyl group in the ion-immobilized metal oxide particle and the functional group in the elastomer.

The ion-immobilized elastomer may be formed from the above-described sol that contains the ion-immobilized metal oxide particle and the anion, which is the counterpart of the cation immobilized to the metal oxide particle. Specifically, a mixed solution in which the sol and the elastomer having the functional group reactive with the hydroxyl group are dissolved in a solvent is applied onto a substrate and then heated. By the heating, the hydroxyl group on the surface of the ion-immobilized metal oxide particle reacts with the functional group in the elastomer, whereby the ion-immobilized metal oxide particle is immobilized (i.e., chemically bonded) to the elastomer. Thus, the ion-immobilized elastomer is produced. In the ion-immobilized elastomer, the ion-immobilized metal oxide particle works also as a crosslinker to crosslink the elastomer. The elastomer may be crosslinked further by another crosslinker.

Examples of the solvent to prepare the mixed solution include pure acetylacetone and a mixed solvent containing acetylacetone, as a main component, and a polar solvent such as 2-methoxyethanol, methyl ethyl ketone, methyl isobutyl ketone, and THF.

The elastomer is not particularly limited as long as it has a functional group reactive with a hydroxyl group. Examples of the functional group include a carboxyl group (—COOH), an amino group (—NH), and an epoxy group. For example, in view of having a high dielectric constant, preferable examples of the elastomer include a carboxylic-modified nitrile rubber (X-NBR) and a carboxylic-modified hydrogenated nitrile rubber (XH-NBR). Among them, an elastomer having an acrylonitrile content (i.e., AN bond amount) of 33 mass % or more is particularly preferable. AN bond amount is defined as amass ratio of acrylonitrile with the entire mass of the rubber being 100 mass %.

The ion-immobilized elastomer may be used to form a dielectric layer of a transducer or a solid polymer electrolyte. The ion-immobilized elastomer preferably has a dielectric constant of 100 or higher, and more preferably 1000 or higher, when measured at a frequency of 0.01 Hz, in view of the use as a dielectric material. Further, the ion-immobilized elastomer preferably has a volume resistivity of $1 \times 10^{12}$ Ω·cm or lower, and more preferably $5 \times 10^{11}$ Ω·cm or lower, in view of having the dielectric constant in the specific range. The volume resistivity is measured in accordance with JIS K 6271 (2008). For the measurement, a direct-current voltage of 100 V is applied to the materials. The ion-immobilized elastomer that contains the reactive ionic liquid according to the preferred embodiment of the present invention may provide the dielectric constant and the volume resistivity in the ranges described above.

Next, a description of a transducer according to a preferred embodiment of the present invention will be provided.

The transducer contains a high-resistance dielectric layer, an ion-immobilized layer, and a pair of electrodes.

Figure 1:
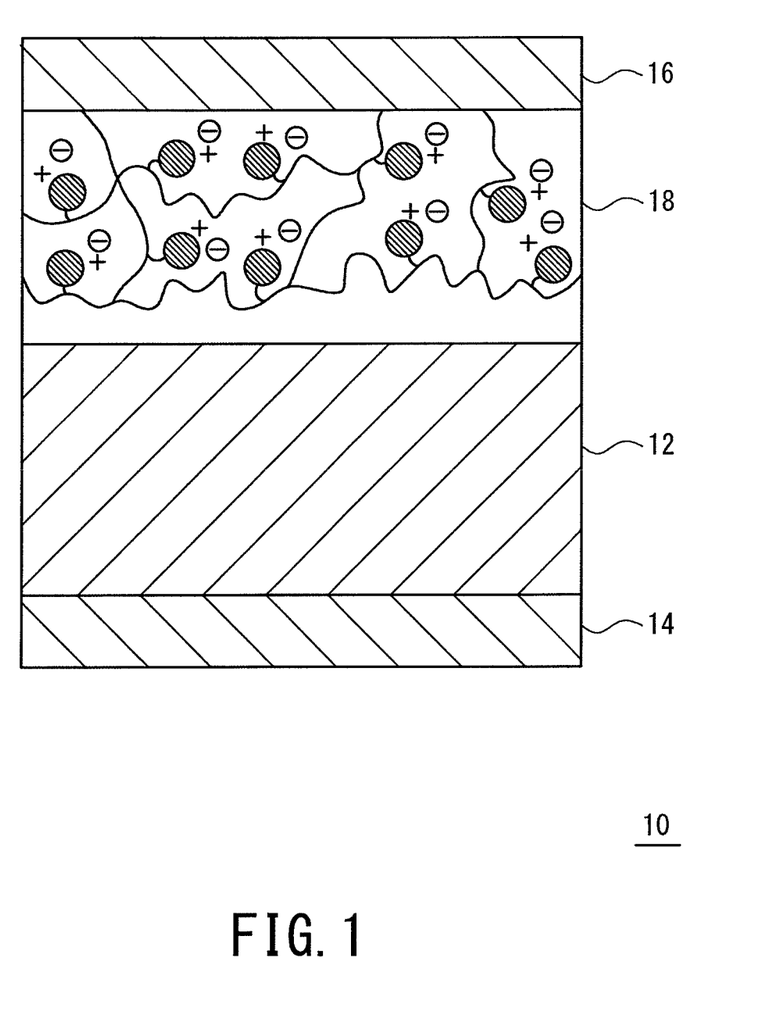
FIG. 1 is a schematic cross-sectional view showing a transducer according to a preferred embodiment of the present invention.

FIG. 1 shows an example of a layer structure of the transducer. The transducer 10 contains a high-resistance dielectric layer 12 and a pair of electrodes 14, 16, placed on the front and back sides of the high-resistance dielectric layer 12, respectively. An ion-immobilized layer 18 made of the ion-immobilized elastomer according to the preferred embodiment of the present invention is placed between the high-resistance dielectric layer 12 and the positive electrode 16. Meanwhile, the negative electrode 14 is in direct contact with the high-resistance dielectric layer 12 with no other dielectric layer placed between them.

The high-resistance dielectric layer 12 contains an elastomer and has a volume resistivity of $10^{13}$ Ω·cm or higher. The high-resistance dielectric layer 12 may be made of the elastomer alone, or may contain other ingredients in addition to the elastomer.

Preferable examples of the elastomer contained in the high-resistance dielectric layer 12 include an ethylene-propylene-diene copolymer (EPDM), an isoprene rubber, a natural rubber, a fluororubber, a nitrile rubber (NBR), a hydrogenated nitrile rubber (H-NBR), a silicone rubber, a urethane rubber, an acrylic rubber, a butyl rubber, a styrene-butadiene rubber, an ethylene-vinyl acetate copolymer, and an ethylene-vinyl acetate-acrylic acid ester copolymer. The examples also include an elastomer modified by, for example, introduction of a functional group such as an epoxidized natural rubber and a carboxylic-modified hydrogenated nitrile rubber (XH-NBR). The elastomers may be used singly or in combination.

Examples of other ingredients contained in the high-resistance dielectric layer 12 include an inorganic filler that has a high insulating property. Addition of an insulating material increases the electric resistance of the high-resistance dielectric layer 12. Examples of the inorganic filler include silica, titanium oxide, barium titanate, calcium carbonate, a clay, a calcined clay, a talc, and a layered clay mineral. They may be used singly or in combination. For example, silica is preferable among them, because silica has a large number of the below-described functional groups, and because silica is relatively inexpensive. When silica or titanium oxide is used, they may be prepared by hydrolysis and polycondensation (i.e., sol-gel reaction) of an organometallic compound. A particle that is prepared by hydrolysis and polycondensation (i.e., sol-gel reaction) of two or more kinds of organometallic compounds, such as barium titanate, may also be used.

In order to increase the insulating property of the high-resistance dielectric layer 12 by blocking a flow of electrons, it is preferable that the elastomer and the inorganic filler are chemically bonded to each other. To form the chemical bond, both the elastomer and the inorganic filler preferably have functional groups that are reactive with each other. Examples of the functional groups include hydroxyl (—OH), carboxyl (—COOH), and maleic anhydride groups. In this case, an elastomer modified, for example, by introduction of a functional group such as a carboxylic-modified hydrogenated nitrile rubber may be used preferably. Functional groups may be introduced to the inorganic filler or be increased in number in the filler by selection of an appropriate production method or by a surface treatment after produced. Having larger numbers of functional groups, the elastomer and the inorganic filler have higher reactivity with each other.

The content of the inorganic filler may be determined in view of a factor such as the volume resistivity of the elastomer. For example, the content is preferably 5 parts by mass or higher and 50 parts by mass or lower with respect to 100 parts by mass of the elastomer. When the content is lower than 5 parts by mass, the electric resistance of the layer 12 is not increased effectively. On the other hand, when the content is higher than 50 parts by mass, the layer 12 may be too hard to maintain sufficient flexibility.

The content of the ion-immobilized particles in the ion-immobilized layer 18 is preferably 1 part by mass or higher and 10 parts by mass or lower with respect to 100 parts by mass of the elastomer. When the content is lower than 1 part by mass, the electrostatic attraction between the electrodes 14, 16 are not effectively increased. On the other hand, when the content is higher than 10 parts by mass, the effect of increasing the electrostatic attraction is saturated while so-called leakage current is increased.

It is preferable that the pair of electrodes 14, 16 can expand and contract following deformation of the high-resistance dielectric layer 12 and the ion-immobilized layer 18. Then, the deformation of the layers 12, 18 is hardly restricted by the electrodes 14, 16, and thus the transducer 10 tends to provide a desired output easily.

The material of the electrodes 14, 16 is not limited specifically. For example, the electrodes 14, 16 may be made from a conductive paste or coating in which a conductive material is mixed in a binder such as an oil and an elastomer. Examples of the conductive material include a carbon material such as carbon black, Ketjen black, carbon nanotube, and graphene, and powders of a metal such as silver. Alternatively, the electrodes 14, 16 may be made of woven meshes of carbon fibers or metal fibers.

The transducer 10 may be produced as follows: a mixed solution to form the ion-immobilized layer 18 is applied onto a substrate, and then is crosslinked by heating. Thus, the ion-immobilized layer 18 is prepared. The high-resistance dielectric layer 12 is prepared similarly; specifically, a solution to form the layer 12 is applied onto a substrate, and then is crosslinked by heating. Next, the high-resistance dielectric layer 12 and the ion-immobilized layer 18 thus prepared are bonded to each other, and the substrates are peeled off. Thus, a laminate of the high-resistance dielectric layer 12 and the ion-immobilized layer 18 is prepared. Further, the electrodes 14, 16 are attached on the front and back sides of the laminate, whereby the transducer 10 is produced.

Figure 2:
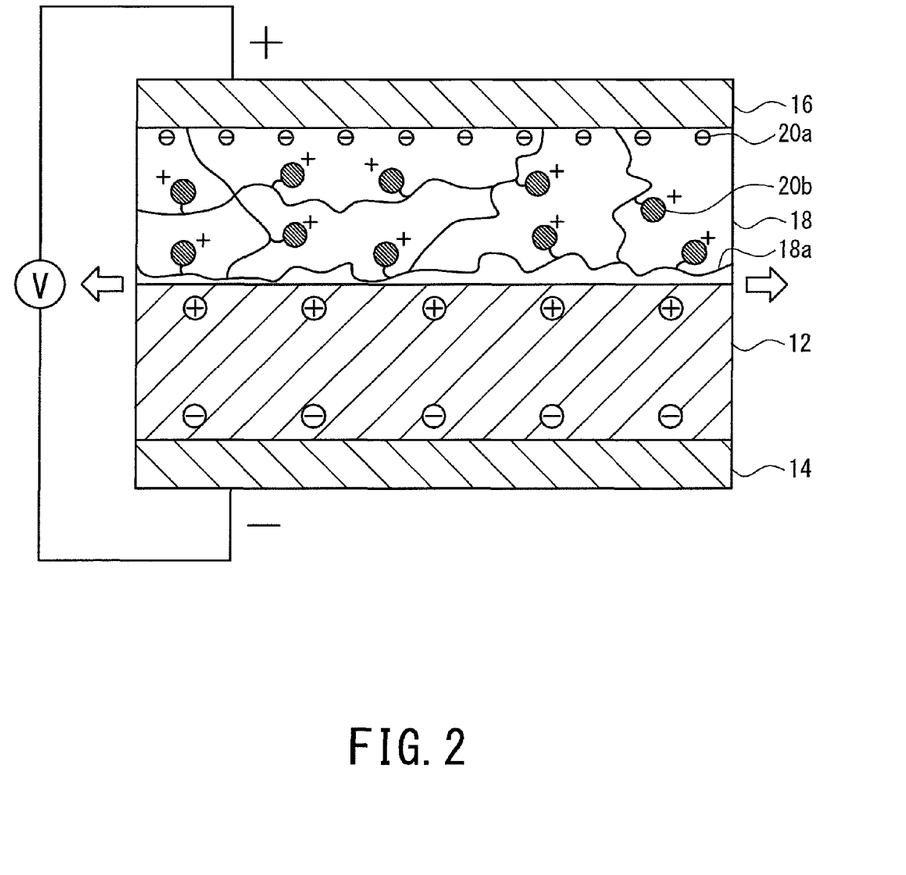
FIG. 2 is a schematic cross-sectional view showing the same during application of a voltage.

As illustrated in FIG. 2, when a voltage is applied between the positive electrode 16 and the negative electrode 14 of the transducer 10, the non-immobilized anions 20a of the reactive ionic liquid in the ion-immobilized layer 18 migrate toward the positive electrode 16. Meanwhile, the cations 20b of the reactive ionic liquid immobilized to the metal oxide particles hardly migrate because the ion-immobilized metal oxide particles are immobilized to the elastomer. In the high-resistance dielectric layer 12, negative electric charges are accumulated in the vicinity of the interface with the negative electrode 14 while positive electric charges are accumulated in the vicinity of the interface with the ion-immobilized layer 18, due to polarization. Thus, a large electrostatic attraction is generated between the positive electrode 16 and the negative electrode 14 that compresses the ion-immobilized layer 18 and the high-resistance dielectric layer 12. As a result, the ion-immobilized layer 18, and the high-resistance dielectric layer 12 are compressed between the electrodes 14, 16 while expanded along the planes of the dielectric layers 12, 18 as illustrated by the white arrows in FIG. 2.

Since the high-resistance dielectric layer 12 has a high electric resistance, the accumulated electric charges do not easily migrate within the high-resistance dielectric layer 12. Therefore, so-called leakage current is low, and generation of Joule heat due to the leakage current is suppressed. In the ion-immobilized layer 18, the cations 20b, having the same polarity as the adjacent positive electrode 16, are immobilized to the elastomer 18a via the metal oxide particles. Therefore, the cations 20b do not easily migrate toward the high-resistance dielectric layer 12 (i.e., toward a side opposite to the positive electrode 16).

Thus, since the ionic component in the ion-immobilized layer 18 consists of a reactive ionic liquid, the ionic component is immobilized to the elastomer 18a in the layer 18 via the metal oxide particle, whereby migration of the ionic component from the ion-immobilized layer 18 to the high-resistance dielectric layer 12 is suppressed. Consequently, decrease of the electric resistance and progress of degradation with time are suppressed in the high-resistance dielectric layer 12, whereby the high-resistance dielectric layer 12 maintains high resistance to dielectric breakdown.

In the transducer 10 described above, while the ion-immobilized layer 18 is placed between the high-resistance dielectric layer 12 and the positive electrode 16, the negative electrode 14 is in direct contact with the high-resistance dielectric layer 12 with no other dielectric layer between them. In view of further increasing the electrostatic attraction between the electrodes 14, 16, an ion-containing layer may be placed also between the high-resistance dielectric layer 12 and the negative electrode 14. In the ion-containing layer, an anion may not be immobilized to an elastomer; however, when the anion is immobilized to the elastomer, migration of the ionic component to the high-resistance dielectric layer 12 is suppressed also from the ion-containing layer placed between the high-resistance dielectric layer 12 and the negative electrode 14 to the high-resistance dielectric layer 12. The anion may be immobilized in the ion-containing layer to the elastomer via a metal-oxide particle with the use of a reactive ionic liquid through immobilization of the anion, as in the case of the cation immobilized in the ion-immobilized layer 18. The reactive ionic liquid used for the immobilization of the anion may have an alkoxysilyl group as a reactive group in the anion structure that reacts with a hydroxyl group contained in the metal oxide particle.

EXAMPLE

A description of the present invention will now be specifically provided with reference to examples.

<Synthesis of Reactive Ionic Liquid 1>

4.78 mL of purified water and then 5.86 g (0.020 mol) of lithium bis(trifluoromethanesulfonyl)imide were added into methacroylcholine chloride (ca. 80% in water; 6.25 g (0.024 mol)). In several minutes, separation of a water-insoluble liquid was observed in the mixture. The mixture was stirred overnight at room temperature. The product was rinses with purified water five times, and then was vacuum-dried. Thus, a viscous ionic liquid monomer was obtained. Then, a methoxysilane group was introduced into the cationic moiety of the monomer by an ene-thiol reaction. Specifically, 4.52 g (10.0 mmol) of the obtained ionic liquid monomer and 2.06 g (10.5 mmol) of 3-mercaptopropyltrimethoxysilane were dissolved in 20 mL of (super dehydrated) methanol. Diisopropylamine was added into the solution as a catalyst in an amount of 20 mol % with respect to the 3-mercaptopropyltrimethoxysilane. The mixture was stirred at room temperature for 20 hours, and then the solvent was removed by evaporation. Thus, reactive ionic liquid 1, represented by structural formula (11) below, was obtained.

(11)

<Synthesis of Reactive Ionic Liquid 2>

18.8 g (0.13 mol) of 2-(dimethylamino)ethyl acrylate and 23.4 g (0.17 mol) of 4-bromobutane were added into 60 mL of acetonitrile, and the mixture was stirred at room temperature for five days. Then, the solvent was removed by evaporation. The product was rinsed with ethyl acetate three times, and then was vacuum-dried. Thus, a hygroscopic solid was obtained. 12.8 g (45.6 mmol) of the solid was dissolved in 50 mL of acetonitrile. Further, an equimolar amount of lithium bis(trifluoromethylsulfonyl)imide was added into the solution, and the mixture was stirred until the bis(trifluoromethylsulfonyl)imide was dissolved. After the mixture was stirred for two hours, the solvent was removed by evaporation. The product was rinsed with purified water three times, and then was vacuum-dried. Thus, a viscous ionic liquid monomer was obtained. Then, an ene-thiol reaction was conducted in the same way as in the synthesis of reactive ionic liquid 1 except that 5.60 g (10.0 mmol) of the obtained ionic liquid monomer and 2.16 g (11.0 mmol) of 3-mercaptopropyltrimethoxysilane were used. Thus, reactive ionic liquid 2, represented by structural formula (12) below, was obtained.

(12)

<Synthesis of Reactive Ionic Liquid 3>

16.3 mL of dichloromethane solution in which 14.8 g (0.163 mol) of acryloyl chloride was dissolved was gradually added at 0° C. into 81.6 mL of a dichloromethane solution in which 22.4 g (0.179 mol) of 2-bromoethanol was resolved. The mixed solution was stirred for 30 minutes. Then, a dichloromethane solution in which 18.2 g (0.179 mol) of triethylamine was dissolved was gradually dropped into the solution. The mixed solution was stirred for several minutes at the temperature, and then was stirred overnight at room temperature. Then, the product was collected by filtration, and was rinsed with 100 mL of purified water three times. Further, anhydrous magnesium sulfate was added into the product. The mixture was stirred for one hour, and then was filtered. Then, the solvent was removed by evaporation. Thus, 2-bromoethyl acrylate was obtained. 13.9 g (0.112 mol) of 1-butylimidazole and 20.0 g (0.112 mol) of the obtained 2-bromoethyl acrylate were added into 30 mL of acetonitrile, and the mixture was stirred at room temperature for five days. The solvent was removed by evaporation, and the product was rinsed with ethyl acetate. After decantation, the product was vacuum-dried. Thus, 2-(1-butylimidazolium-3-yl)ethyl acrylate bromide was obtained. 20.0 g (0.0659 mol) of the compound and 18.9 g (0.0659 mol) of lithium bis(trifluoromethylsulfonyl)imide were added into 72 mL of acetonitrile. The mixture was stirred for one hour. Then, the solvent was removed by evaporation, and the product was rinsed with purified water four times. The water was removed by evaporation. Then, ethyl acetate was added into the product, and the mixture was filtered. The product was vacuum-dried again. Thus, an ionic liquid monomer was obtained. An ene-thiol reaction was conducted in the same way as in the synthesis of reactive ionic liquid 1 except that 5.03 g (10.0 mmol) of the obtained ionic liquid monomer and 2.16 g (11.0 mmol) of 3-mercaptopropyltrimethoxysilane were used. Thus, reactive ionic liquid 3, represented by structural formula (13) below, was obtained.

(13)

<Synthesis of Reactive Ionic Liquid 4>

20.0 g (0.0816 mol) of 2-bromoethylphosphonate diethyl and 6.7 g (0.0816 mol) of 1-methylimidazole were added into 30 mL of acetonitrile. The mixture was stirred at room temperature for five days, and then the solvent was removed by evaporation. The product was rinsed with ethyl acetate, and was vacuum-dried. Thus, a viscous product was obtained. 10.0 g (0.0305 mol) of the viscous product was dissolved in 30 mL of acetonitrile. Further, an equimolar amount of lithium bis(trifluoromethylsulfonyl)imide was added into the solution, and the mixture was stirred until the bis(trifluoromethylsulfonyl)imide was dissolved. After the solution was stirred at room temperature for three days, the solvent was removed by evaporation. Then, purified water and chloroform were added into the product and the chloroform layer was rinsed with water five times. The solvent was removed by evaporation, and ethyl acetate was added into the product. Then, the product was collected by filtration and, and was vacuum-dried again. Thus, reactive ionic liquid 4, represented by structural formula (14) below, was obtained.

(14)

<Synthesis of Reactive Ionic Liquid 5>

10.0 g (0.070 mol) of 2-(dimethylamino)ethyl acrylate was put into a 100-mL flask. 12.6 g (0.077 mol) of methyl trifluoromethanesulfonate was dropped into the flask slowly at 0° C. The mixture was stirred. As the stirring proceeded, solidification of the mixture was observed. Then, hexane was added into the flask at room temperature, and the mixture was stirred for 1.5 hours. The hexane supernatant was removed by evaporation. Then, the product was rinsed with hexane again, and was vacuum-dried. An ene-thiol reaction was conducted in the same way as in the synthesis of reactive ionic liquid 1 except that 3.07 g (10.0 mmol) of the obtained ionic liquid monomer and 2.16 g (11.0 mmol) of 3-mercaptopropyltrimethoxysilane were used and that the acetonitrile was used as a solvent. Thus, reactive ionic liquid 5, represented by structural formula (15) below, was obtained.

(15)

<Synthesis of Reactive Ionic Liquid 6>

10.0 g (0.0357 mol) of the solid obtained during the synthesis of reactive ionic liquid 2 and 7.0 g (0.0439 mol) of methyl trifluoromethanesulfonate were stirred at room temperature. As the reaction proceeded, a viscous liquid was produced. The stirring was continued for two hours, and then, an excess of the methyl trifluoromethanesulfonate was removed by evaporation. An ene-thiol reaction was conducted in the same way as in the synthesis of reactive ionic liquid 1 except that 3.49 g (10.0 mmol) of the obtained ionic liquid monomer and 2.16 g (11.0 mmol) of 3-mercaptopropyltrimethoxysilane were used. Thus, reactive ionic liquid 6, represented by structural formula (16) below, was obtained.

(16)

<Synthesis of Reactive Ionic Liquid 7>

5.0 g (0.053 mol) of vinylimidazole was suspended in 20 mL of hexane, and 8.71 g (0.053 mol) of methyl trifluoromethanesulfonate was dropped into the suspension slowly at 0° C. The mixture was stirred overnight at room temperature. Then, an excess of the methane trifluoromethanesulfonate was removed by evaporation. Thus, a viscous product was obtained. An ene-thiol reaction was conducted in the same way as in the synthesis of reactive ionic liquid 13 except that 5.0 g (19.4 mmol) of the obtained ionic liquid monomer, 4.18 g (21.3 mmol) of 3-mercaptopropylt-rimethoxysilane, and 70 mL of (super dehydrated) methanol were used. Thus, reactive ionic liquid 7, represented by structural formula (17) below, was obtained.

(17)

<Synthesis of Reactive Ionic Liquid 8>

20.8 g (0.22 mol) of vinylimidazole and 9.4 g (0.29 mol) of 4-bromobutane were stirred with 66 mL of acetonitrile at room temperature for five days. Then, the solvent was removed by evaporation. The product was rinsed with ethyl acetate five times, and was vacuum-dried. Thus, a viscous fluid was obtained. Then, 7.3 g (0.0445 mol) of methyl trifluoromethanesulfonate was dropped into 10 g (0.0433 mol) of the obtained viscous fluid slowly at 20° C. Since a stirrer could not be rotated at a low temperature, the mixture was vibrated at room temperature until the stirrer was rotated. The stirring was continued for 1.5 hours. An excess of the methyl trifluoromethanesulfonate was removed by evaporation. Thus, a viscous liquid was obtained. An ene-thiol reaction was conducted in the same way as in the synthesis of reactive ionic liquid 13 except that 3.5 g (11.6 mmol) of the obtained ionic liquid monomer and 2.52 g (12.8 mmol) of 3-mercaptopropyltrimethoxysilane were used. Thus, reactive ionic liquid 8, represented by structural formula (18) below, was obtained.

(18)

<Synthesis of Reactive Ionic Liquid 9>

3.04 g (0.0185 mol) of methyl trifluoromethanesulfonate was dropped into 5.05 g (0.0154 mol) of the viscous product obtained during the synthesis of reactive ionic liquid 4 at a low temperature, and the mixture was stirred for 30 minutes at the low temperature and for 1.5 hours at room temperature. The product was rinsed with hexane. Then, an excess of the methyl trifluoromethanesulfonate was removed by evaporation. Thus, reactive ionic liquid 9, represented by structural formula (19) below, was obtained.

(19)

<Synthesis of Reactive Ionic Liquid 10>

12.16 g (0.0979 mol) of 1-butylimidazole and 20.0 g (0.0816 mol) of 2-bromoethylphosphonate diethyl were dissolved in 30 mL of acetonitrile, and the solution was stirred at room temperature for four days. Then, the solvent was removed by evaporation, and the product was rinsed with diethyl ether twice. 2.66 g (0.0163 mol) of methyl trifluoromethanesulfonate was added into 5 g (0.0135 mol) of the obtained liquid, and the mixture was stirred for 30 minutes. Then, an excess of the methyl trifluoromethanesulfonate was removed by evaporation. Thus, reactive ionic liquid 10, represented by structural formula (20) below, was obtained.

(20)

<Synthesis of Reactive Ionic Liquid 11>

1.92 g (0.020 mol) of methanesulfonic acid was dropped into 15.0 g of a solution of 1-methyl-3-vinylimidazolium methyl carbonate (solvent: methanol/water mixture; concentration: 25 mass %; 0.020 mol). The mixture was stirred at room temperature for one hour. Then, the solvent was removed by evaporation, and the product was vacuum-dried for two hours. An ene-thiol reaction was conducted in the same way as in the synthesis of reactive ionic liquid 13 except that 3.00 g (14.7 mmol) of the obtained ionic liquid monomer and 3.17 g (16.1 mmol) of 3-mercaptopropyltrimethoxysilane were used. Thus, reactive ionic liquid 11, represented by structural formula (21) below, was obtained.

(21)

<Synthesis of Reactive Ionic Liquid 12>

10.0 g (0.070 mol) of 2-(dimethylamino)ethyl acrylate was put in a 100-mL flask, and 9.83 g (0.077 mol) of methyl trifluoroacetate was dropped into the flask slowly at 0° C. The mixture was stirred for 1.5 hours at the temperature, and for two hours at room temperature. Then, an excess of the methylrifluoroacetate was removed by evaporation. The product was rinsed with hexane, and was vacuum-dried. Thus, a precipitated solid was obtained. An ene-thiol reaction was conducted in the same way as in the synthesis of reactive ionic liquid 1 except that 2.71 g (10.0 mmol) of the obtained ionic liquid monomer and 2.16 g (11.0 mmol) of 3-mercaptopropyltrimethoxysilane were used. Thus, reactive ionic liquid 12 represented by structural formula (22) below, was obtained.

(22)

<Synthesis of Reactive Ionic Liquid 13>

2.32 g (0.020 mol) of trifluoroacetic acid was dropped into 15.0 g of a solution of 1-methyl-3-vinylimidazolium methyl carbonate (solvent: methanol/water mixture; concentration: 25 mass %; 0.020 mol) slowly at a low temperature. Generation of bubbles was observed during the dropping. The mixture was returned to room temperature in 30 minutes, and stirred for 1.5 hours. Then, the solvent was removed by evaporation, and the product was vacuum-dried for two hours. Since an ene-thiol reaction with the use of an amine catalyst did not proceed, an ene-thiol reaction by radical addition was conducted. Specifically, 3.0 g (13.5 mmol) of the obtained ionic liquid monomer produced by the reaction and 2.92 g (14.9 mmol) of 3-mercaptopropyltrimethoxysilane were added into 40 mL of (super dehydrated) methanol. Azobisisobutyronitrile was added into the mixture as a radical generator in an amount of 15 mol % with respect to the 3-mercaptopropyltrimethoxysilane. Then, Argon (Ar) bubbles were introduced into the mixture for 30 minutes, and then the mixture was refluxed in Ar at 75° C. for seven hours. Then, the solvent was removed by evaporation. The product was rinsed with diethyl ether, and was vacuum-dried. Thus, reactive ionic liquid 13, represented by structural formula (23) below, was obtained.

(23)

<Synthesis of Reactive Ionic Liquid 14>

3.26 g (0.054 mol) of acetic acid was dropped into 40.0 g of a solution of 1-methyl-3-vinylimidazolium methyl carbonate (solvent: methanol/water mixture; concentration: 25 mass %; 0.054 mol). The mixture was stirred at room temperature for two hours. Then, the solvent was removed by evaporation, and the product was vacuum-dried for two hours. An ene-thiol reaction was conducted in the same way as in the synthesis of reactive ionic liquid 13 except that 3.36 g (20.0 mmol) of the obtained ionic liquid monomer and 4.32 g (22.0 mmol) of 3-mercaptopropyltrimethoxysilane were used. Thus, reactive ionic liquid 14 represented by structural formula (24) below, was obtained.

(24)

<Synthesis of Reactive Ionic Liquid 15>

3.80 g (0.020 mol) of p-toluenesulfonic acid monohydrate was dropped into 15.0 g of a solution of 1-methyl-3-vinylimidazolium methyl carbonate (solvent: methanol/wa- ter mixture; concentration: 25 mass %; 0.020 mol). The mixture was stirred at room temperature for one hour. Then, the solvent was removed by evaporation, and the product was vacuum-dried for two hours. An ene-thiol reaction was conducted in the same way as in the synthesis of reactive ionic liquid 13 except that 3.00 g (10.7 mmol) of the obtained ionic liquid monomer and 2.31 g (11.8 mmol) of 3-mercaptopropyltrimethoxysilane were used. Thus, reactive ionic liquid 15 represented by structural formula (25) below, was obtained.

(25)

<Synthesis of Reactive Ionic Liquid 16>

3.80 g (0.022 mol) of benzenesulfonic acid monohydrate was dropped into 16.2 g of a solution of 1-methyl-3-vinylimidazolium methyl carbonate (solvent: methanol/water mixture; concentration: 25 mass %; 0.022 mol). The mixture was stirred at room temperature for one hour. Then, the solvent was removed by evaporation, and the product was vacuum-dried for two hours. An ene-thiol reaction was conducted in the same way as in the synthesis of reactive ionic liquid 13 except that 3.00 g (11.3 mmol) of the obtained ionic liquid monomer and 2.43 g (12.4 mmol) of 3-mercaptopropyltrimethoxysilane were used. Thus, reactive ionic liquid 16 represented by structural formula (26) below, was obtained.

(26)

<Synthesis of Reactive Ionic Liquid 17>

15.0 g (81.0 mmol) of 2-(diethylamino)ethyl methacrylate (DEAM) was added into 60 mL of THF. Further, 12.6 g (89.0 mmol) of methyl iodide was dropped into the mixture at 0° C. In several minutes, the solution began to turn whitish. The solution was stirred for one hour, and then a solid portion was collected by filtration. Further, the filtrate was cooled, and a precipitated solid was collected by filtration. Thus, an iodide salt [DEAM] [I], represented by structural formula (27) below, was obtained.

1.27 g (5.5 mmol) of silver oxide and 1.94 g (11.0 mmol) of benzenesulfonic acid monohydrate was added into 100 mL of purified water, and the mixture was stirred at 60° C. for one hour. 3.61 g (11.0 mmol) of the iodide salt [DEAM] [I] was added into the mixture, and then the mixture was stirred overnight in dark. Then, a precipitate (i.e., AgI) was removed by filtration, and a spatula of activated charcoal was added into the obtained filtrate. The mixture was stirred for one hour. Then, the activated charcoal was removed by filtration, and moisture was removed by evaporation. Thus, a viscous solid was obtained. An ene-thiol reaction was conducted in the same way as in the synthesis of reactive ionic liquid 1 except that 3.00 g (8.39 mmol) of the obtained ionic liquid monomer and 1.81 g (9.23 mmol) of 3-mercaptopropyltrimethoxysilane were used. Thus, reactive ionic liquid 17 represented by structural formula (28) below, was obtained.

(27)

(28)

<Synthesis of Reactive Ionic Liquid 18>

20.0 g (0.0816 mol) of diethyl 2-bromoethylphosphonate and 6.7 g (0.0816 mol) of 1-methylimidazole were added into 30 mL of acetonitrile. The mixture was stirred at room temperature for five days. Then, the solvent was removed by evaporation. The product was rinsed with ethylacetate, and was vacuum-dried. Thus, a viscous product (bromine salt) was obtained. 9.8 g (0.030 mol) of the viscous product (bromine salt) was dissolved in 10 mL of ethanol, and the solution was added into an ethanol solution of an equimolar amount (i.e., 5.0 g (0.030 mol)) of silver acetate (ethanol content: 20 mL). The mixture was stirred overnight at room temperature, and was filtered. Then, the filtrate was stirred with activated charcoal for two hours. Then, the mixture was filtered. The solvent in the filtrate was removed by evaporation, and the product was vacuum-dried. Thus, reactive ionic liquid 18, represented by structural formula (29) below, was obtained.

(29)

<Synthesis of Reactive Ionic Liquid 19>

The iodide salt [DEAM] [I] was obtained in the same way as in the synthesis of reactive ionic liquid 17.

2.77 g (11.9 mmol) of silver oxide and 4.0 g (23.9 mmol) of 4-nitrobenzoic acid were added into 170 mL of dehy- drated methanol, and the mixture was stirred for two hours. Then, 7.83 g (23.9 mmol) of the iodide salt [DEAM] [I] was added into the mixture, and the resulting mixture was stirred overnight in dark. A precipitate (i.e., AgI) was removed by filtration, and a spatula of activated charcoal was added into the obtained filtrate. The mixture was stirred for two hours. Then, the activated charcoal was removed by filtration, and the methanol in the filtrate was removed by evaporation. Thus, a solid product was obtained. An ene-thiol reaction was conducted in the same way as in the synthesis of reactive ionic liquid 1 except that 3.00 g (8.18 mmol) of the obtained ionic liquid monomer and 1.77 g (9.00 mmol) of 3-mercaptopropyltrimethoxysilane were used. Thus, reactive ionic liquid 19 represented by structural formula (30) below, was obtained.

(30)

<Synthesis of Reactive Ionic Liquid 20>

2.77 g (11.9 mmol) of silver oxide and 4.0 g (23.9 mmol) of 4-nitrobenzoic acid were added into 170 mL of dehydrated methanol, and the mixture was stirred for two hours. Then, 6.21 g of aqueous solution of methacroylcholine chloride (ca. 80%; 23.9 mmol) was added to the mixture, and the obtained mixture was stirred overnight at room temperature. The resulting mixture was filtered, and a spatula of activated charcoal was added into the obtained filtrate. The mixture was stirred for two hours. Then, the activated charcoal was removed by filtration, and the methanol in the filtrate was removed by evaporation. Thus, a solid product was obtained. An ene-thiol reaction was conducted in the same way as in the synthesis of reactive ionic liquid 1 except that 3.00 g (8.86 mmol) of the obtained ionic liquid monomer and 1.91 g (9.75 mmol) of 3-mercaptopropyltrimethoxysilane were used. Thus, reactive ionic liquid 20 represented by structural formula (31) below, was obtained.

(31)

<Synthesis of Reactive Ionic Liquid 21>

10.0 g (52.9 mmol) of sodium 3-nitrobenzoate was added into 190 mL of dehydrated methanol, and the mixture was stirred. Then, 13.73 g (52.9 mmol) of aqueous solution of methacroylcholine chloride (ca. 80%; 52.9 mmol) was added into the mixture, and the obtained mixture was stirred overnight at room temperature. The mixture was filtered, and a spatula of activated charcoal was added into the obtained filtrate. The mixture was stirred for two hours. Then, the activated charcoal was removed by filtration, and the methanol in the filtrate was removed by evaporation. Thus, a solid product was obtained. An ene-thiol reaction was conducted in the same way as in the synthesis of reactive ionic liquid 1 except that 3.00 g (8.86 mmol) of the obtained ionic liquid monomer and 1.91 g (9.75 mmol) of 3-mercaptopropyltrimethoxysilane were used. Thus, reactive ionic liquid 21 represented by structural formula (32) below, was obtained.

(32)

<Synthesis of Ion-Immobilized Metal Oxide Particles>

The obtained reactive ionic liquids were each resolved in 1:1 mixture (in molar ratio) of titanium tetraisopropoxide and acetylacetone. Isopropyl alcohol was further added into the solutions. Then, hydrolysis was carried out by dropping of water four times as much as the titanium tetraisopropoxide in molar ratio. Thus, sols in which cations of the reactive ionic liquids were immobilized to titanium dioxide particles. The sample according to Comparative Example 4 was prepared with no ionic liquid added to the metal oxide particles.

<Synthesis of Ion-Immobilized Elastomer>

The obtained sols were each mixed in a 12-mass % solution of a carboxylic-modified hydrogenated nitrile rubber (HX-NBR; "Therban TX8889", manufactured by Lanxess) in acetylacetone so that the ion-immobilized metal oxide particles equivalent to 2.4 parts by mass of $TiO_2$ may be contained in each of the mixtures with respect to 100 parts by mass of the HX-NBR. Further, 5 parts by mass of an acetylacetone solution of tetrakis(2-ethylhexyloxy) titanium (concentration: 20 mass %) was added into the mixtures as a crosslinker. The obtained mixed solutions were each applied onto substrates to form 9 μm thick films. The films were dried at 150° C. for one hour. Thus, ion-immobilized elastomers were obtained.

<Preparation of Actuator>

(High-Resistance Dielectric Layer)

[$TiO_2$ Sol]

0.01 mol of tetra-i-propoxy titanium, which is an organometallic compound, was chelated with 0.02 mol of acetylacetone. Then, 0.083 mol of isopropyl alcohol (IPA), 0.139 mol of methyl ethyl ketone (MEK), and 0.04 mol of water were added to the obtained chelated compound. Thus, a sol containing $TiO_2$ particles was obtained. Then, the obtained sol was left for two hours at 40° C. for aging. The obtained sol is called a $TiO_2$ sol.

[$TiO_2/ZrO_2$ Sol]

In the same process as in the above-described preparation of the $TiO_2$ sol, a chelated product prepared by chelating of 0.005 mol of zirconium alkoxide with 0.01 mol of acetylacetone was added to the chelated product of the tetra-1-propoxy titanium, and then the IPA, MEK, and water were added to the mixture. Thus, a sol containing $TiO_2/ZrO_2$ composite particles was obtained. Then, the obtained sol was left for two hours at 40° C. for aging. The obtained sol is called a $TiO_2/ZrO_2$ sol.

A polymer solution having a solid content concentration of 12 mass % was prepared by dissolving a carboxylic-modified hydrogenated nitrile rubber ("Therban™ XT8889", manufactured by Lanxess) in acetylacetone. Then, 20.57 parts by mass of the $TiO_2$ sol, 13.23 parts by mass of the $TiO_2/ZrO_2$ sol, and 3 parts by mass of an acetylacetone solution of tetrakis(2-ethylhexyloxy) titanium, as a crosslinker, were added into 100 parts by mass of the polymer solution. Thus, a mixed solution was prepared. The mixed solution was applied onto a substrate and dried, and then, heated at 150° C. for about 60 minutes. Thus, a high-resistance dielectric layer was obtained. The thickness of the high-resistance dielectric layer was about 20 μm, the volume resistivity thereof was $3 \times 10^{14}$ Ω·cm, and the content of the $TiO_2$ and $TiO_2/ZrO_2$ particles were 6.6 and 5.82 parts by mass, respectively, with respect to 100 parts by mass of the elastomer (i.e., HX-NBR).

(Preparation of Actuator)

In order to evaluate properties of the ion-immobilized elastomers alone, a dielectric layer (dielectric film) consisting only of an ion-immobilized layer made of each of the above-prepared ion-immobilized elastomers was prepared, instead of a double-layered dielectric layer consisting of the high-resistance dielectric layer and the ion-immobilized layer. Here, an elastomer layer without immobilized ions was used for Comparative Example 4, instead of the ion-immobilized elastomer. Carbon black was mixed and dispersed in an acrylic rubber solution to prepare a conductive coating. The conductive coating was screen-printed onto both the front and back sides of the prepared dielectric layer to provide electrodes. Thus, an actuator was obtained.

For the materials of the dielectric layers (i.e., ion-immobilized elastomers) according to Examples and Comparative Examples, ion immobilization rates, volume resistivities, dielectric constants, and actuator properties were evaluated. Methods and results of the evaluations are illustrated below. Configurations of the materials of the dielectric layers are described in Tables. In Tables, the content ratios are represented by parts by mass. The amounts of the reactive ionic liquid in Tables represent amounts of the reactive ionic liquids that were used in the synthesis of the ion-immobilized metal oxide particles, by mmol.

(Ion Immobilization Rate)

The ion-immobilized elastomers were each immersed in an extractant (ethanol) for 24 hours. The amount of the extractant was 50 g per 1 g of the samples. The immersion was carried out three times for a single sample. Then, the extractants collected after the immersion were analyzed with TOF-MS. Measurements were conducted on the collected extractants and reference samples. Each of the reference samples consists of an ionic liquid/extractant solution with a known concentration. Concentration of the ionic liquid in each of the extractants (i.e., ion concentration in the extractant) was calculated based on a ratio of peak areas of the cationic moiety in measured spectra between the extractant and the corresponding reference sample (see formula 1). Further, an ion amount in the extractant was calculated based on the calculated value of the concentration of the ionic liquid and the amount of the extractant (see formula 2). Then, an immobilization rate was estimated based on the ion amount in the extractant and the amount of ions that was used for preparation of the sample (i.e., initial ion amount).

$$\text{Ion Concentration in Extractant} = \frac{\text{Concentration of Reference} \times \text{Peak Area of Extractant}}{\text{Peak Area of Reference}} \quad \text{(Formula 1)}$$

$$\text{Ion Amount in Extractant} = \text{Ion Concentration in Extractant} \times \text{Amount of Extractant} \quad \text{(Formula 2)}$$

$$\text{Immobilization Rate} = \frac{\text{Initial Ion Amount} - \text{Ion Amount in Extractant}}{\text{Initial Ion Amount}} \times 100 \quad \text{(Formula 3)}$$

(Volume Resistivity)

Volume resistivities of the materials of the dielectric layers were measured in accordance with JIS K6271 (2008). For the measurement, a direct-current voltage of 100 V was applied to the materials.

(Dielectric Constant)

The materials of the dielectric layers were each mounted on a sample holder ("12962A", manufactured by Solartron). Then, dielectric constants of the materials were measured with a dielectric interface ("1296", manufactured by Solartron) and a frequency response analyzer ("1255B", manufactured by Solartron) in combination (frequency: 0.01 Hz).

(Actuator Property)

Figure 3:
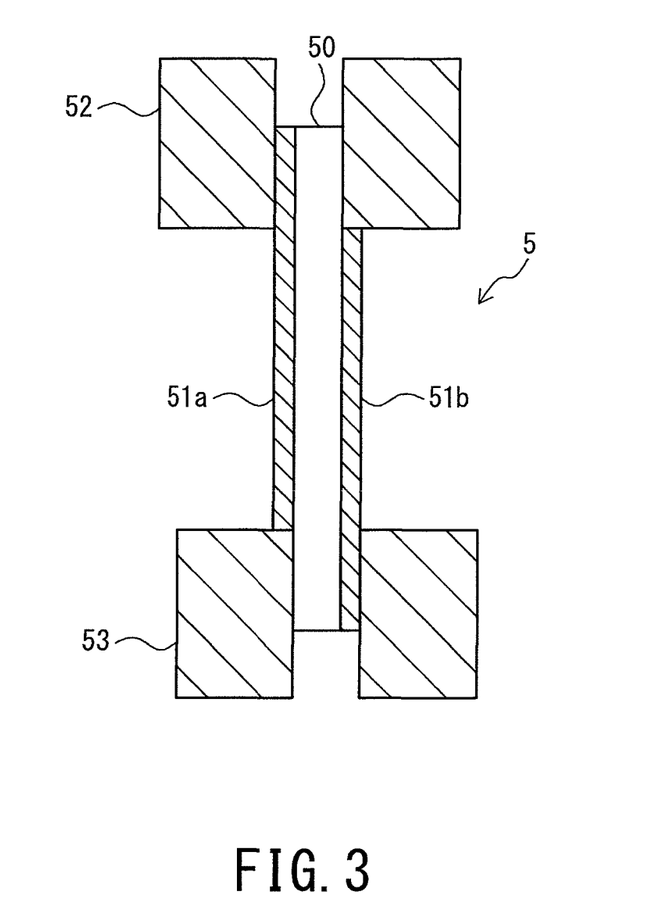
FIG. 3 is a cross-sectional view showing an actuator mounted on a measurement apparatus.

For the actuators prepared above, generative stresses were measured. The generative stresses, which represent actuator properties, were measured while a direct-current voltage with a field intensity of 25 V/μm was applied. FIG. 3 shows a cross-sectional view of an actuator mounted on a measurement apparatus.

As illustrated in FIG. 3, the upper end of an actuator 5 was held by an upper chuck 52 of the measuring apparatus. The lower end of the actuator 5 was held by a lower chuck 53. The actuator 5 was mounted between the upper chuck 52 and the lower chuck 53 while being extended in advance in the vertical direction (elongation ratio: 25%). A load cell (not shown) was arranged above the upper chuck 52.

The actuator 5 included a dielectric layer 50 and a pair of electrodes 51a, 51b. The electrodes 51a, 51b were arranged on the front and back sides of the dielectric layer, respectively, facing each other. Each of the electrodes 51a, 51b had a rectangular plate shape that was 40 mm long, 25 mm wide, and about 10 μm thick in a natural state. The electrodes 51a, 51b were arranged so as to be displaced from each other by 10 mm in the vertical direction. In other words, the electrodes 51a, 51b overlapped each other, via the dielectric layer 50, in an area of 30 mm long and 25 mm wide. An electric wire (not shown) was connected to the lower end of the electrode 51a. Similarly, an electric wire (not shown) was connected to the upper end of the electrode 51b. The electrodes 51a, 51b were connected to a power source (not shown) through the respective electric wires.

When a voltage was applied between the electrodes 51a, 51b, an electrostatic attraction occurred between the electrodes 51a, 51b to compress the dielectric layer 50. The dielectric layer 50 thereby decreased in thickness and expanded in the extension direction (i.e., in the vertical direction). Through the expansion of the dielectric layer 50, the extension stress in the vertical direction decreased. A decrease in the extension stress during the voltage application was measured with the load cell and was regarded as a generative stress.

(Ion Retention Rate)

The actuators were immersed in ethanol, which can dissolve the ionic liquids, overnight. Then, the actuators were taken out of the ethanol, and rinsed with ethanol. In these processes, ions that were not immobilized in the actuators were extracted out. Generative stresses of the actuators were measured before and after the extraction processes while a direct-current voltage with a field intensity of 30 V/μm was applied. Ion retention rates of the actuators were evaluated as the ratios of the generative stresses.

TABLE 1

| | Example | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Rubber Polymer | 100 | 100 | 100 | 100 | 100 | 100 | 100 | 100 | 100 | 100 | 100 | 100 | 100 |
| Crosslinker | 5 | 5 | 5 | 5 | 5 | 5 | 5 | 5 | 5 | 5 | 5 | 5 | 5 |
| Titanium Oxide Particles | 1.65 | 1.65 | 1.65 | 1.65 | 1.65 | 1.65 | 1.65 | 1.65 | 1.65 | 1.65 | 1.65 | 1.65 | 1.65 |
| Reactive Ionic Liquid 1 | 0.39 | | | | | | | | | | | | |
| Reactive Ionic Liquid 2 | | 0.39 | | | | | | | | | | | |
| Reactive Ionic Liquid 3 | | | 0.39 | | | | | | | | | | |
| Reactive Ionic Liquid 4 | | | | 0.39 | | | | | | | | | |
| Reactive Ionic Liquid 5 | | | | | 0.39 | | 0.78 | 1.56 | | | | | |
| Reactive Ionic Liquid 6 | | | | | | 0.39 | | | | | | | |
| Reactive Ionic Liquid 7 | | | | | | | | | 0.39 | | | | |
| Reactive Ionic Liquid 8 | | | | | | | | | | 0.39 | | | |
| Reactive Ionic Liquid 9 | | | | | | | | | | | 0.39 | | |
| Reactive Ionic Liquid 10 | | | | | | | | | | | | 0.39 | |
| Reactive Ionic Liquid 11 | | | | | | | | | | | | | 2.73 |
| Reactive Ionic Liquid 12 | | | | | | | | | | | | | |
| Reactive Ionic Liquid 13 | | | | | | | | | | | | | |
| Reactive Ionic Liquid 14 | | | | | | | | | | | | | |
| Dielectric Constant (0.01 Hz) | 5000 | 4000 | 3300 | 1500 | 1900 | 2400 | 3600 | 12000 | 1200 | 2200 | 2500 | 2600 | 230 |
| Volume Resistivity (Ω · cm) | $3 \times 10^{11}$ | $3 \times 10^{11}$ | $5 \times 10^{11}$ | $8 \times 10^{11}$ | $8 \times 10^{11}$ | $8 \times 10^{11}$ | $4 \times 10^{11}$ | $2 \times 10^{11}$ | $7 \times 10^{11}$ | $5 \times 10^{11}$ | $4 \times 10^{11}$ | $5 \times 10^{11}$ | $2 \times 10^{12}$ |
| Generative Stress (MPa) | 0.30 | 0.28 | 0.26 | 0.27 | 0.32 | 0.35 | 0.45 | 0.52 | 0.41 | 0.43 | 0.31 | 0.43 | 0.07 |
| Ion Immobilization Rate (%) | | | | | 99 | | | | 91 | | | | |
| Generative Stress Before Extraction (MPa): A | | | | | 0.45 | | | | | 0.53 | 0.59 | | |
| Generative Stress After Extraction (MPa): B | | | | | 0.43 | | | | | 0.48 | 0.52 | | |
| Ion Retention Rate (B/A) × 100 (%) | | | | | 95 | | | | | 91 | 87 | | |

TABLE 2

| | Example | | | | | | Comparative Example | | | | |
|---|---|---|---|---|---|---|---|---|---|---|---|
| | 14 | 15 | 16 | 17 | 18 | 19 | 1 | 2 | 3 | 4 | 5 |
| Rubber Polymer | 100 | 100 | 100 | 100 | 100 | 100 | 100 | 100 | 100 | 100 | 100 |
| Crosslinker | 5 | 5 | 5 | 5 | 5 | 5 | 5 | 5 | 5 | 5 | 5 |
| Titanium Oxide Particles | 1.65 | 1.65 | 1.65 | 1.65 | 1.65 | 1.65 | 1.65 | 1.65 | 1.65 | 1.65 | 1.65 |
| Reactive Ionic Liquid 12 | | | | | | | 0.39 | | | | |
| Reactive Ionic Liquid 13 | | | | | | | | 0.39 | | | |
| Reactive Ionic Liquid 14 | | | | | | | | | 0.39 | | |
| Reactive Ionic Liquid 15 | 2.73 | | | | | | | | | | |
| Reactive Ionic Liquid 16 | | 2.73 | | | | | | | | | |
| Reactive Ionic Liquid 17 | | | 2.73 | | | | | | | | |
| Reactive Ionic Liquid 18 | | | | | | | | | | | 0.39 |
| Reactive Ionic Liquid 19 | | | | 2.73 | | | | | | | |
| Reactive Ionic Liquid 20 | | | | | 2.73 | | | | | | |
| Reactive Ionic Liquid 21 | | | | | | 2.73 | | | | | |
| Dielectric Constant (0.01 Hz) | 620 | 580 | 3600 | 4200 | 60 | 70 | 20 | 20 | 20 | 20 | 23 |
| Volume Resistivity (Ω · cm) | $4 \times 10^{11}$ | $6 \times 10^{11}$ | $1 \times 10^{11}$ | $4 \times 10^{11}$ | $5 \times 10^{11}$ | $4 \times 10^{11}$ | $1 \times 10^{13}$ | $1 \times 10^{13}$ | $1 \times 10^{13}$ | $1 \times 10^{13}$ | $1 \times 10^{13}$ |
| Generative Stress (MPa) | 0.25 | 0.26 | 0.35 | 0.09 | 0.21 | 0.19 | 0.06 | 0.06 | 0.06 | 0.06 | 0.06 |
| Ion Immobilization Rate (%) | 99 | 99 | | | | | | | | | |
| Generative Stress Before Extraction (MPa): A | 0.45 | 0.46 | | | | | | | | | |
| Generative Stress After Extraction (MPa): B | 0.43 | 0.44 | | | | | | | | | |
| Ion Retention Rate (B/A) × 100 (%) | 95 | 96 | | | | | | | | | |

In Comparative Example 4, the material of the dielectric layer has a high resistivity and a low dielectric constant since no ionic liquid is contained in the material. Accordingly, the actuator has a small generative stress. In Comparative Examples 1 to 3, and 5, the materials of the dielectric layers have high resistivities and low dielectric constants since ionic liquids that contain carboxylate anions (except nitrobenzoate anions) are used. Accordingly, the actuators have small generative stresses. Thus, the materials of the dielectric layers according to Comparative Examples 1 to 5 provide poor actuator properties.

Meanwhile, the materials of the dielectric layers according to Examples 1 to 19 have low resistivities and high dielectric constants since the materials contain anions selected from sulfonate, sulfonylimide, and nitrobenzoate (i.e., $CF_3SO_3^-$, $CH_3SO_3^-$, $CH_3C_6H_4SO_3^-$, $C_6H_5SO_3^-$, $(CF_3SO_2)_2N^-$, 3-nitrobenzoate, and 4-nitrobenzoate) anions. Accordingly, the actuators have large generative stresses. Thus, the materials of the dielectric layers according to Examples 1 to 19 provide excellent actuator properties. Further, the materials have high ion immobilization ratios since the reactive ionic liquids contain cations having specific structures. Thus, in the materials, migration of ions from the ion-immobilized layers to the high-resistance dielectric layers on application of the voltage is suppressed.

The ion-immobilized elastomer according to the preferred embodiment of the present invention is useful for an actuator, a sensor, and a power generating device, which perform conversion between mechanical energy and electric energy. The elastomer is also useful for a speaker, a microphone, and a transducer such as of a noise canceller, which perform conversion between acoustic energy and electric energy. It is particularly useful for a flexible actuator, which is used for an artificial muscle for an industrial, medical, or welfare robots; for a small-sized pump used for cooling of the electronic devices or used in the medical field; and for a medical instrument.

The foregoing description of the preferred embodiments of the present invention has been presented for purposes of illustration and description; however, it is not intended to be exhaustive or to limit the present invention to the precise form disclosed, and modifications and variations are possible as long as they do not deviate from the principles of the present invention.

The invention claimed is:

1. An ion-immobilized metal oxide particle that is prepared by a process comprising reacting a metal oxide particle with a reactive ionic liquid comprising an ion pair that consists of an anion and a cation,
   (a) the cation:
      (a1) being an imidazolium or quaternary ammonium cation; and
      (a2) comprising a reactive group that consists of an alkoxysilyl or phosphonate group;
   (b) the anion:
      (b1) being a sulfonate or nitrobenzoate anion;
   the ion-immobilized metal oxide particle comprising:
      the cation; and
      a metal oxide particle comprising a hydroxyl group,
   the cation being immobilized to the metal oxide particle via an Si—O or P—O bond between the reactive group of the cation and the hydroxyl group of the metal oxide particle.

2. An ion-immobilized elastomer comprising:
   the ion-immobilized metal oxide particle according to claim 1; and
   an elastomer that comprises a functional group that is reactive with a hydroxyl group,
   the ion-immobilized metal oxide particle being immobilized to the elastomer via a bond between a hydroxyl group contained in the ion-immobilized metal oxide particle and the functional group contained in the elastomer.

3. A transducer comprising:
   a high-resistance dielectric layer that comprises an elastomer and has a volume resistivity of $10^{13}$ Ω·cm or higher;
   a pair of positive and negative electrodes that are arranged on front and back sides of the high-resistance dielectric layer; and
   an ion-immobilized layer arranged between the high-resistance dielectric layer and the positive electrode, the ion-immobilized layer comprising the ion-immobilized elastomer according to claim 2.

4. The ion-immobilized metal oxide particle according to claim 1,
   wherein the cation having a structure represented by one selected from formulae (1) to (3):

where, in formulae (1) to (3), $R_1$ to $R_{11}$ are straight-chain or branched alkyl groups that either comprise or do not comprise heteroatoms, and at least a part of the plurality of $R_4$ are either identical to or different from one another.

5. An ion-immobilized elastomer comprising
   the ion-immobilized metal oxide particle according to claim 4, and
   an elastomer that comprises a functional group that is reactive with a hydroxyl group,
   the ion-immobilized metal oxide particle being immobilized to the elastomer via a bond between a hydroxyl group contained in the ion-immobilized metal oxide particle and the functional group contained in the elastomer.

6. A transducer comprising:
   a high-resistance dielectric layer that comprises an elastomer and has a volume resistivity of $10^{13}$ Ω·cm or higher;
   a pair of positive and negative electrodes that are arranged on front and back sides of the high-resistance dielectric layer; and
   an ion-immobilized layer arranged between the high-resistance dielectric layer and the positive electrode, the ion-immobilized layer comprising the ion-immobilized elastomer according to claim 5.

7. The ion-immobilized metal oxide particle according to claim 1, wherein the anion is one selected from $CH_3SO_3^-$, $CH_3C_6H_4SO_3^-$, $C_6H_5SO_3^-$, 3-nitrobenzoate anion, and 4-nitrobenzoate anion.

8. The ion-immobilized metal oxide particle according to claim 1,
wherein the cation having a structure represented by one selected from formulae (1) to (3):

where, in formulae (1) to (3), $R_1$ to $R_{11}$ are straight-chain or branched alkyl groups that either comprise or do not comprise heteroatoms, and at least a part of the plurality of $R_4$ are either identical to or different from one another; and
wherein the anion is one selected from $CH_3SO_3^-$, $CH_3C_6H_4SO_3^-$, $C_6H_5SO_3^-$, 3-nitrobenzoate anion, and 4-nitrobenzoate anion.

9. An ion-immobilized elastomer comprising:
the ion-immobilized metal oxide particle according to claim 8; and
an elastomer that comprises a functional group that is reactive with a hydroxyl group,
the ion-immobilized metal oxide particle being immobilized to the elastomer via a bond between a hydroxyl group contained in the ion-immobilized metal oxide particle and the functional group contained in the elastomer.

10. A transducer comprising:
a high-resistance dielectric layer that comprises an elastomer and has a volume resistivity of $10^{13}$ Ω·cm or higher;
a pair of positive and negative electrodes that are arranged on front and back sides of the high-resistance dielectric layer; and
an ion-immobilized layer arranged between the high-resistance dielectric layer and the positive electrode, the ion-immobilized layer comprising the ion-immobilized elastomer according to claim 9.

* * * * *